(12) United States Patent
Boegli

(10) Patent No.: US 8,449,926 B2
(45) Date of Patent: May 28, 2013

(54) TOPICAL ANTIFUNGAL COMPOSITION

(75) Inventor: Charles J. Boegli, Cincinnati, OH (US)

(73) Assignee: Onikolabs LLC, Cincinnati, OH (US)

( * ) Notice: Subject to any disclaimer, the term of this patent is extended or adjusted under 35 U.S.C. 154(b) by 0 days.

(21) Appl. No.: 12/830,803

(22) Filed: Jul. 6, 2010

(65) Prior Publication Data

US 2011/0008474 A1    Jan. 13, 2011

Related U.S. Application Data

(60) Provisional application No. 61/223,870, filed on Jul. 8, 2009.

(51) Int. Cl.
*A61K 36/00* (2006.01)
*A61K 36/53* (2006.01)

(52) U.S. Cl.
USPC .......................................... 424/725; 424/745

(58) Field of Classification Search
None
See application file for complete search history.

(56) References Cited

U.S. PATENT DOCUMENTS

2006/0073211 A1 * 4/2006 Marenick et al. ............. 424/581

FOREIGN PATENT DOCUMENTS

| WO | WO 96/37210 | 11/1996 |
|---|---|---|
| WO | WO 2004/076680 | 9/2004 |
| WO | WO 2005/087244 | 9/2005 |

OTHER PUBLICATIONS

Dalleau, S. et al., "In vitro activity of essential oils and their major components against *Candida albicans* yeasts growing planktonically and as biofilms," International Journal of Antimocrobial Agents, vol. 29(2) (Mar. 2007) and 17th European Congress of Clinical Microbiology and Infectious Diseases, Munich, Germany (Mar. 31-Apr. 3, 2007) p. S147 (Abstracts).

International Search Report dated Mar. 30, 2011 for Application No. PCT/US2010/041050.

Kalemba, D. et al., "Antibacterial and Antifungal properties of Essential Oils," Current Medicinal Chemistry, vol. 10(10) (Jan. 1, 2003) pp. 813-829, Table 4 (Abstract).

Didry, N. et al., "Activity of thymol, carvacrol, cinnamaldehyde and eugenol on oral bacteria," Pharm. Acta. Helv., vol. 69(1) (Jul. 1994) pp. 25-28.

Manohar, V. et al., "Antifungal activities of origanum oil against *Candida albicans*," Molecular and Cellular Biochemistry, vol. 228 (2001) pp. 111-117.

* cited by examiner

*Primary Examiner* — Qiuwen Mi
(74) *Attorney, Agent, or Firm* — Jenei LLC

(57) ABSTRACT

A composition obtained primarily from plant materials provides antimicrobial activity for use as an anti-fungal agent. The anti-fungal agent is effective in inhibiting the growth of *Trichophyton rubrum*, the fungus that is the most common cause of Tinea pedis. The composition includes selective mixtures of the *origanum* oil, menthol, and Atlantic cedarwood oil, *thuja* oil, cedarwood oil, cinnamon oil, clove oil, cumin oil, fennel oil, peppermint oil, or rosemary oil.

22 Claims, No Drawings

TOPICAL ANTIFUNGAL COMPOSITION

BACKGROUND OF THE INVENTION

Many of the commonly used antimicrobial agents are synthetic compounds. In recent years, there has been an increased interest in avoiding or eliminating the use of synthetic compounds and in developing and promoting the use of natural materials. Consumers generally consider plant materials less toxic and a more suitable natural alternative to synthetic compounds.

Various herbal and plant preparations are known for certain uses. For example, Listerine® antiseptic mouthwash is a known composition containing thyme oil, eucalyptus oil, methyl salicylate (wintergreen oil), and menthol in an alcohol solution. This composition is produced as an oral hygiene composition. Various reports have been produced showing Listerine® causes a reduction in plaque and gingivitis. Although various other plant compositions have been produced, many of the commercially available compositions have not shown substantial antimicrobial activity.

The body normally serves as host for a variety of bacteria and fungi. Most of the time, the balance between the body as host and the microorganisms is maintained. Sometimes, however, conditions exist that permit the microorganisms to tip that balance, causing an infection. Such fungi are only problematic when they grow in an uncontrolled manner, causing various diseases as well as discomfort for the infected human or animal. Unfortunately, uncontrolled fungal growths regularly occur, making topical anti-fungal preparations one of the largest segments of the market for topical external products.

Once fungal populations have become uncontrolled, the resultant infection is difficult to treat successfully. Synthetic topical antifungal preparations are commonly used for treatment. However, such infections are often recurrent and require a prolonged treatment regimen. Some consumers find prolonged treatment using synthetic products undesirable.

Certain fungal infections of the skin known as tinea infections are caused by dermatophytes, which are members of the *Trichophyton*, *Microsporum* and *Epidermophyton* species. These mold-like fungi thrive in warm, moist areas, thriving on the dead tissues of hair, nails, and outer skin layers. Tinea infections include tinea pedis, known as athlete's foot; tinea corporis, known as ringworm; tinea capitis, a fungal infection of the scalp that can cause hair loss; tinea cruris, known as jock itch or tinea of the groin; tinea unguum, which is tinea of the nails; and tinea versicolor, a superficial fungal infection that produces brown, tan, or white spots on the trunk of the body. Tinea infections are contagious and can be passed through direct contact or by contact with clothing, from shower and pool surfaces, and even from pets.

Athlete's foot or tinea pedis is by far the most common form, with more than 12 million people in the United States suffering from the disease per year. It presents with redness, itching, burning, cracking, scaling, swelling and occasionally bleeding. The condition generally includes small vesicles, fissures, scaling, maceration, hyperkeratinization, and eroded areas between the toes and on the plantar surface of the foot, as well as on other skin areas. The nails may show thickening, pitting and subungal debris. Local antifungals include imidazoles, such as miconazole nitrate and clotrimazole, tolnaftate, and terbinafine hydrochloride. The common fungicidal and fungistatic chemical treatments frequently fail to contact the fungi in the horny layers of the skin, which means athlete's foot slowly clears with local antifungal therapy or systemic antifungals. This requires the infected individual to take treatments for considerable lengths of time, potentially for months. Common treatments for athlete's foot using local antifungals require treatment two or three times a day for at least 7 to 14 days, and for some medications, for up to four weeks. It is common treatment to apply the topical antifungal for two weeks after the skin is healed, to eradicate all remaining fungal spores. Physicians commonly prescribe medications in the form of powders, aerosols, liquids or creams for the treatment of tinea pedis.

However, reoccurrences of the infection are frequent. For some patients, such as those also afflicted with diabetes or circulatory problems, tinea infections and their treatment can be quite serious. The source of the affliction often is a public safety and health concern, as the occurrence of tinea pedis is higher in public areas such as locker rooms, public showers, sports facilities, and the like.

Increasingly, herbal remedies are sought due to concerns caused by antibiotic-resistant and other drug-resistant infectious agents. Even with herbal treatments, however, numerous difficulties are encountered in the treatment of medical conditions. A single herb may contain numerous active, and sometimes conflicting, components. The common herb, rhubarb, for example, may be used in small doses for treating constipation due to its tannic acid component, but is a potent laxative in larger doses because of other components. Other herbs, such as black walnut extract, which may be used to treat athlete's foot and related fungal infections, can be toxic if taken inappropriately. In addition to those difficulties mentioned in connection with single herbs, combinations raise the possibility of deleterious effects among components in the various herbs, and increase the difficulties associated with anticipating and analyzing side effects.

BRIEF SUMMARY OF THE INVENTION

The present invention relates generally to an antimicrobial composition obtained from plant materials, plant extracts, essential oils obtained from the plant materials, and synthetic compounds. One embodiment of the present invention relates generally to a composition of *origanum* oil in combination with additional plant materials, plant extracts, essential oils, or synthetic compounds. Another embodiment relates to a composition of peppermint oil with additional plant materials, plant extracts, essential oils, or synthetic compounds.

A general embodiment of the present invention is an antimicrobial composition. In another embodiment of the invention, the antimicrobial composition contains a mixture of the plant materials, plant extracts or oils, or synthetic compounds in amounts effective to inhibit the growth of microorganisms. In one embodiment of the invention, the composition is an anti-fungal.

In one embodiment, the invention provides for a composition of *origanum* oil and menthol. In another embodiment, the invention provides for a composition comprising at least about 80% *origanum* oil and at least about 5% menthol.

In another embodiment, the invention provides for a composition comprising at least about 80%, 85%, or 90% *origanum* oil. In another embodiment of the invention, the composition comprises at most about 85%, 90%, 95%, or 98% *origanum* oil.

In another embodiment, the invention provides for a composition comprising at least about 3%, 5%, 10%, or 15% menthol. In another embodiment of the invention, the composition comprises at most about 10%, 15%, or 20% menthol.

In one embodiment of the invention, the menthol is a synthetic product. In another embodiment of the invention, the menthol is obtained from peppermint or other mint oils. In another embodiment, the menthol is obtained as a menthol crystal.

In another embodiment of the invention, concentrations of menthol are from about 5% to about 20%.

In another embodiment of the invention, the composition comprises one or more phenolic compounds, such as carvacrol or thymol, and one or more secondary alcohols, such as menthol. In one embodiment, the composition comprises at least 40% of one or more phenolic compounds and at least 3% of one or more secondary alcohols.

In another embodiment, the invention provides for a composition comprising at least about 50%, 60%, or 70% of one or more phenolic compounds. In another embodiment, the invention provides for a composition comprising at most about 60%, 70%, 80%, or 90% of one or more phenolic compounds, such as carvacrol or thymol.

In another embodiment, the invention provides for a composition comprising at least about 5%, 7%, or 10% of one or more secondary alcohols. In another embodiment, the invention provides for a composition comprising at most about 10%, 15%, or 20% of one or more secondary alcohols.

In a further embodiment of the invention, the composition includes *origanum* oil and menthol and also includes the essential oils of at least one of the following: *thuja*, cedarwood, cinnamon, clove, cumin, fennel, peppermint, or rosemary. In one embodiment of the invention, the composition comprises at least about 75% *origanum* oil; at least about 3% menthol; and at least about 3% of at least one of the essential oils of: *thuja* oil, cedarwood oil, cinnamon, clove, cumin, fennel, mint, peppermint, or rosemary.

In another embodiment, the invention provides for a composition comprising at least about 3%, 5% or 10% of the essential oils of at least one of the following: *thuja*, cedarwood, cinnamon, clove, cumin, fennel, peppermint, or rosemary. In another embodiment, the invention provides for a composition comprising at most about 10%, 15% or 20% of the essential oils of at least one of the following: *thuja*, cedarwood, cinnamon, clove, cumin, fennel, mint, peppermint, or rosemary.

In one embodiment, the invention provides for a composition of *origanum* oil and Atlantic cedarwood oil. In another embodiment, the invention provides for a composition comprising at least 85% *origanum* oil and at least 5% Atlantic cedarwood oil.

In another embodiment, the invention provides for a composition comprising at least about 85%, 90%, or 95% *origanum* oil. In another embodiment, the invention provides for a composition comprising at most about 90%, 93%, or 95% *origanum* oil.

In another embodiment, the invention provides for a composition comprising at least about 5%, 7%, or 10% Atlantic cedarwood oil. In another embodiment, the invention provides for a composition comprising at most about 5%, 10%, or 15% Atlantic cedarwood oil.

In another embodiment of the invention, concentrations of Atlantic cedarwood oil are from about 5% to about 10%.

In another embodiment of the invention, the composition comprises at least 50% of one or more phenolic compounds, such as carvacrol or thymol; and at least about 0.4% of one or more terpene hydrocarbons, such as the alpha-himachalene, beta-himachalene, or gamma-himachalene.

In another embodiment, the invention provides for a composition comprising at least about 50%, 60%, or 70% of one or more phenolic compounds, such as carvacrol or thymol. In another embodiment, the invention provides for a composition comprising at most about 65%, 70%, 80%, or 90% of one or more phenolic compounds, such as carvacrol or thymol.

In another embodiment, the invention provides for a composition comprising at least about 0.04%, 0.1%, 1%, or 3% of one or more terpene hydrocarbons, such as the alpha-himachalene, beta-himachalene, or gamma-himachalene. In another embodiment, the invention provides for a composition comprising at most about 3%, 5%, or 7% of one or more terpene hydrocarbons, such as the alpha-himachalene, beta-himachalene, or gamma-himachalene.

In a further embodiment of the invention, the composition includes *origanum* oil and Atlantic cedarwood oil and also includes the essential oils of at least one of the following: *thuja*, cedarwood, cinnamon, clove, cumin, fennel, mint, peppermint, or rosemary.

In a further embodiment of the invention, the composition comprises at least about 70% *origanum* oil and at least about 3% of the essential oils of at least one of the following: *thuja*, cedarwood, cinnamon, clove, cumin, fennel, mint, peppermint, or rosemary.

In another embodiment, the invention provides for a composition comprising at least about 75%, 85%, or 90% *origanum* oil. In another embodiment, the invention provides for a composition comprising at most about 85%, 90%, 95%, or 97% *origanum* oil.

In another embodiment, the invention provides for a composition comprising at least about 3%, 5%, 10% of the essential oils of at least one of the following: *thuja*, cedarwood, cinnamon, clove, cumin, fennel, mint, peppermint, or rosemary. In another embodiment, the invention provides for a composition comprising at most about 5%, 10%, 15% or 20% of the essential oils of at least one of the following: *thuja*, cedarwood, cinnamon, clove, cumin, fennel, mint, peppermint, or rosemary.

In another embodiment of this invention, the composition comprises *origanum* oil, menthol, and Atlantic cedarwood oil. In another embodiment of this invention, the composition comprises at least about 70% *origanum* oil; at least about 3% menthol, and at least about 3% Atlantic cedarwood oil. In another embodiment of this invention, the composition comprises about 85% *origanum* oil, about 10% menthol, and about 5% Atlantic cedarwood oil.

In another embodiment of the invention, the composition comprises at least about 50% of one or more phenolic compounds, such as carvacrol or thymol; at least about 1% of one or more secondary alcohols, such as menthol; and at least about 0.04% of one or more terpene hydrocarbons, such as alpha-himachalene, beta-himachalene, or gamma-himachalene.

In a further embodiment of the invention, the composition includes *origanum* oil, menthol, and Atlantic cedarwood oil and also includes the essential oils of at least one of the following: *thuja*, cedarwood, cinnamon, clove, cumin, fennel, mint, peppermint, or rosemary.

In another embodiment of this invention, the composition comprises at least about 50% *origanum* oil; at least about 3% menthol; at least about 3% Atlantic cedarwood oil; and at least about 3% of the essential oils of at least one of the following: *thuja*, cedarwood, cinnamon, clove, cumin, fennel, mint, peppermint, or rosemary.

In another embodiment of this invention, the composition comprises at least about 50% *origanum* oil; at least about 3% menthol; at least about 3% Atlantic cedarwood oil; and at least about 3% cedarwood oil.

In another embodiment of this invention, the composition comprises at least about 3%, 5%, or 10% cedarwood oil. In another embodiment of this invention, the composition comprises at most about 5%, 10%, or 15% cedarwood oil.

In another embodiment of this invention, the composition comprises at least about 50% *origanum* oil; at least about 3% menthol; at least about 3% Atlantic cedarwood oil; and at least about 3% *thuja* oil.

In another embodiment of this invention, the composition comprises at least about 3%, 5%, or 10% *thuja* oil. In another embodiment of this invention, the composition comprises at most about 5%, 10%, or 15% *thuja* oil.

In another embodiment of this invention, the composition comprises at least about 50% *origanum* oil; at least about 3% menthol; at least about 3% Atlantic cedarwood oil; and at least about 3% cinnamon oil.

In another embodiment of this invention, the composition comprises at least about 3%, 5%, or 10% cinnamon oil. In another embodiment of this invention, the composition comprises at most about 5%, 10%, or 15% cinnamon oil.

In another embodiment of this invention, the composition comprises at least about 50% *origanum* oil; at least about 3% menthol; at least about 3% Atlantic cedarwood oil; and at least about 3% clove oil.

In another embodiment of this invention, the composition comprises at least about 3%, 5%, or 10% clove oil. In another embodiment of this invention, the composition comprises at most about 5%, 10%, or 15% clove oil.

In another embodiment of this invention, the composition comprises at least about 50% *origanum* oil; at least about 3% menthol; at least about 3% Atlantic cedarwood oil; and at least about 3% cumin oil.

In another embodiment of this invention, the composition comprises at least about 3%, 5%, or 10% cumin oil. In another embodiment of this invention, the composition comprises at most about 5%, 10%, or 15% cumin oil.

In another embodiment of this invention, the composition comprises at least about 50% *origanum* oil; at least about 3% menthol; at least about 3% Atlantic cedarwood oil; and at least about 3% fennel oil.

In another embodiment of this invention, the composition comprises at least about 3%, 5%, or 10% fennel oil. In another embodiment of this invention, the composition comprises at most about 5%, 10%, or 15% fennel oil.

In another embodiment of this invention, the composition comprises at least about 50% *origanum* oil; at least about 3% menthol; at least about 3% Atlantic cedarwood oil; and at least about 3% rosemary oil.

In another embodiment of this invention, the composition comprises at least about 3%, 5%, or 10% rosemary oil. In another embodiment of this invention, the composition comprises at most about 5%, 10%, or 15% rosemary oil. In another embodiment of this invention, the rosemary oil is extracted Moroccan rosemary plants.

In another embodiment of this invention, the composition comprises at least about 50% *origanum* oil; at least about 3% menthol; at least about 3% Atlantic cedarwood oil; and at least about 3% peppermint oil.

In another embodiment of this invention, the composition comprises at least about 3%, 5%, or 10% peppermint oil. In another embodiment of this invention, the composition comprises at most about 5%, 10%, or 15% peppermint oil. In another embodiment of this invention, the peppermint oil is peppermint oil bottom fraction that is obtained from the bottom oil fraction after peppermint distillation.

In another embodiment of this invention, the composition comprises at least about 50% *origanum* oil; at least about 3% menthol; at least about 3% Atlantic cedarwood oil; and at least about 3% mint oil.

In another embodiment of this invention, the composition comprises at least about 3%, 5%, or 10% mint oil. In another embodiment of this invention, the composition comprises at most about 5%, 10%, or 15% mint oil.

In another embodiment of the invention, the composition comprises *origanum* oil, menthol, cumin oil, and clove oil. In one embodiment of the invention, the composition comprises at least about 50% *origanum* oil; at least about 3% menthol; at least about 3% cumin oil; and at least about 3% clove oil.

In another embodiment of the invention, the composition comprises *origanum* oil, menthol, Atlantic cedarwood oil, cumin oil, and clove oil. In one embodiment of the invention, the composition comprises at least about 45% *origanum* oil; at least about 3% menthol; at least about 3% Atlantic cedarwood oil; at least about 3% cumin oil; and at least about 3% clove oil.

In another embodiment of the invention, the composition comprises *origanum* oil, menthol, Atlantic cedarwood oil, cumin oil, clove oil, and cinnamon oil. In one embodiment of the invention, the composition comprises at least about 45% *origanum* oil; at least about 3% menthol; at least about 3% Atlantic cedarwood oil; at least about 3% cumin oil; at least about 3% clove oil; and at least 3% cinnamon oil.

In another embodiment of the invention, the composition comprises *origanum* oil, menthol, Atlantic cumin oil, clove oil, and cinnamon oil. In one embodiment of the invention, the composition comprises at least about 45% *origanum* oil; at least about 3% menthol; at least about 3% cumin oil; at least about 3% clove oil; and at least 3% cinnamon oil.

In another embodiment of the invention, the composition comprises *origanum* oil, menthol, Atlantic cedarwood oil, cumin oil, clove oil, and peppermint oil. In one embodiment of the invention, the composition comprises at least about 45% *origanum* oil; at least about 3% menthol; at least about 3% Atlantic cedarwood oil; at least about 3% cumin oil; at least about 3% clove oil; and at least 3% peppermint oil.

In another embodiment of the invention, the composition comprises *origanum* oil, menthol, cumin oil, clove oil, and peppermint oil. In one embodiment of the invention, the composition comprises at least about 45% *origanum* oil; at least about 3% menthol; at least about 3% cumin oil; at least about 3% clove oil; and at least 3% peppermint oil.

In one embodiment, the invention provides for a composition of peppermint oil bottom fraction and *origanum* oil. In another embodiment, the composition contains at least 40% peppermint oil bottom fraction and at least 40% *origanum* oil.

In one embodiment, the invention provides for a composition of peppermint oil bottom fraction and menthol. In another embodiment, the invention provides for a composition comprising at least about 70% peppermint oil bottom fraction and at least about 5% menthol.

In another embodiment, the invention provides for a composition comprising at least about 60%, 75%, 80%, 85%, or 90% peppermint oil bottom fraction. In another embodiment of the invention, the composition comprises at most about 85%, 90%, 95%, 98%, or 99% peppermint oil bottom fraction.

In a further embodiment of the invention, the composition includes peppermint oil bottom fraction and menthol and also includes the essential oils of at least one of the following: *thuja*, cedarwood, cinnamon, clove, cumin, fennel, mint, or rosemary. In one embodiment of the invention, the composition comprises at least about 75% peppermint oil bottom fraction; at least about 3% menthol; and at least about 3% of at least one of the essential oils of: *thuja*, cedarwood, cinnamon, clove, cumin, fennel, mint, or rosemary In one embodiment, the invention provides for a composition of peppermint oil bottom fraction and Atlantic cedarwood oil. In another embodiment, the invention provides for a composition comprising at least 85% peppermint oil bottom fraction and at least 3% Atlantic cedarwood oil.

In a further embodiment of the invention, the composition comprises at least about 70% peppermint oil bottom fraction and at least about 3% of the essential oils of at least one of the following: *thuja*, cedarwood, cinnamon, clove, cumin, fennel, mint, or rosemary.

In one broad embodiment, the composition includes peppermint oil bottom fraction and one or both of menthol and Atlantic cedarwood oil. In a further embodiment of the invention, the composition can also include the essential oils of *thuja*, cedarwood, cinnamon, clove, cumin, fennel, mint, or rosemary. These preceding additives may be used individually or in combination.

In another embodiment of this invention, the composition comprises peppermint oil bottom fraction, menthol, and Atlantic cedarwood oil. In another embodiment of this invention, the composition comprises at least about 40% peppermint oil bottom fraction; at least about 3% menthol, and at least about 3% Atlantic cedarwood oil. In another embodiment of this invention, the composition comprises about 85% peppermint oil bottom fraction, about 10% menthol, and about 5% Atlantic cedarwood oil.

In a further embodiment of the invention, the composition includes peppermint oil bottom fraction, menthol, and Atlantic cedarwood oil and also includes the essential oils of at least one of the following: thuja, cedarwood, cinnamon, clove, cumin, fennel, mint, or rosemary.

In a further embodiment, the composition includes peppermint oil bottom fraction and eucalyptus. In another embodiment, the composition includes at least 60% peppermint oil bottom fraction; and at least 5% eucalyptus.

In another embodiment of the invention, concentration of eucalyptus oil is at least about 7%, 10%, or 15%. In another embodiment of the invention, concentration of eucalyptus oil is at most about 7%, 10%, 15%, or 20%. In another embodiment of the invention, the concentration of eucalyptus oil is at least about 75%, 80%, or 85% of the total composition. In another embodiment of the invention, the concentration of eucalyptus oil is at most about 80%, 85%, 90%, or 95%.

In another embodiment of the invention, concentration of peppermint oil bottom fraction is at least about 7%, 10%, or 15%. In another embodiment of the invention, concentration of peppermint oil bottom fraction is at most about 7%, 10%, 15%, or 20%.

In a further embodiment, the composition includes peppermint oil bottom fraction and thyme oil. In another embodiment, the composition includes at least 60% peppermint oil bottom fraction; and at least 5% thyme oil.

In another embodiment of the invention, concentration of thyme oil is at least about 7%, 10%, or 15%. In another embodiment of the invention, concentration of thyme oil is at most about 7%, 10%, 15%, or 20%. In another embodiment of the invention, the concentration of thyme oil is at least about 75%, 80%, or 85% of the total composition. In another embodiment of the invention, the concentration of thyme oil is at most about 80%, 85%, 90%, or 95%.

In a further embodiment, the composition includes peppermint oil bottom fraction and fennel oil. In another embodiment, the composition includes at least about 60% peppermint oil bottom fraction; and at least 5% fennel oil.

In another embodiment of the invention, concentration of fennel oil is at least about 7%, 10%, or 15%. In another embodiment of the invention, concentration of fennel oil is at most about 7%, 10%, 15%, or 20%. In another embodiment of the invention, the concentration of fennel oil is at least about 75%, 80%, or 85% of the total composition. In another embodiment of the invention, the concentration of fennel oil is at most about 80%, 85%, 90%, or 95%.

In another embodiment of the invention, the composition consists of Germacrene-D. In another embodiment, the composition consists of at least about 15% Germacrene-D. In another embodiment of the invention, the concentration of Germacrene-D is at least about 20%, 25%, 30%, or 33%. In another embodiment of the invention, the concentration of Germacrene-D is at most about 20%, 25%, 30%, 33%, or 35%.

In a further embodiment, the composition includes Germacrene-D and fennel oil. In another embodiment, the composition includes at least about 15% Germacrene-D and at least 5% fennel oil.

In a further embodiment, the composition includes Germacrene-D and thyme oil. In another embodiment, the composition includes at least 15% Germacrene-D and at least 5% thyme oil.

In a further embodiment, the composition includes Germacrene-D and eucalyptus. In another embodiment, the composition includes at least 15% Germacrene-D and at least 5% eucalyptus.

In one embodiment, the invention provides for a composition of Germacrene-D and menthol. In another embodiment, the invention provides for a composition comprising at least about 15% Germacrene-D and at least about 5% menthol.

In another embodiment of the invention, the composition further comprises an additional antifungal agent selected from the group consisting of miconazole, econazole, ketoconazole, itraconazole, fluconazole, bifoconazole, terconazole, butoconazole, tioconazole, oxiconazole, sulconazole, saperconazole, clotrimazole, isoconazole, butoconazole, clioquinol, lanoconazole, neticonazole, ciclopirox, butenafine, undecylenic acid, haloprogin, tolnaftate, nystatin, ciclopirox olamine, terbinafine, amorolfine, naftifine, elubiol, griseofulvin, corticosteroids, amphotericin, calcipotriene, anthraline, minoxidil, minoxidil sulfate, retinoids, cysteine, acetyl cysteine, methionine, glutathione, biotin, finasteride and ethocyn, tea tree oil, mupirocin, neomycin sulfate bacitracin, polymyxin B, I-ofloxacin, chlortetracycline hydrochloride, oxytetracycline hydrochloride, tetracycline hydrochloride, clindamycin phosphate, gentamicin sulfate, benzalkonium chloride, benzethonium chloride, hexylresorcinol, methylbenzethonium chloride, phenol, quaternary ammonium compounds, triclocarbon, triclosan, flucytosine, salicylic acid, fezatione, ticlatone, triacetin, zinc pyrithione and sodium pyrithione, mixtures thereof, pharmaceutically acceptable salts thereof and mixtures of pharmaceutically acceptable salts thereof.

In another embodiment of the invention, the composition further comprises a penetration enhancer selected from the group consisting of an alkali metal alkyl sulfate, glycerin, a bile acid or bile salt, lecithin, hyaluronic acid, octylphenoxypolyethoxyethanol, glycolic acid, lactic acid, chamomile extract, cucumber extract, oleic acid, linolenic acid, borage oil, evening primrose oil, polyglycerin, lysine, polylysine, triolein, monoolein, monooleates, monolaurates, menthol, polidocanol alkyl ethers, chenodeoxycholate, deoxycholate and pharmaceutically acceptable salts and analogues thereof; wherein the penetration enhancer is present in a concentration of 0.1 to 10 w/w % based on the total weight of the preparation. In a further embodiment of the invention, the penetration enhancer may be present in an amount of between about 0.1 to about 5 percent by weight of the total composition, in an amount of between about 0.5 to about 4 percent by weight of the total composition and in an amount of between about 1 to about 2 percent by weight of the total composition.

In one embodiment of the invention, the composition further comprises an antioxidant in an amount of between about 0.5 to about 10 percent by weight of the total composition, in an amount of between about 1 to about 2 percent by weight of the total composition, and wherein the antioxidant comprises ascorbyl palmitate, alpha tocopherol, butylated hydroxyanisole or fumaric acid.

In one embodiment of this invention, the composition is undiluted. In another embodiment of this invention, the composition is diluted in an oil selected from the group consisting of almond oil, borage oil, canola oil, grape seed oil, jojoba oil, olive oil, soybean oil, sunflower oil, wheat germ oil, apricot kernel oil, carrot oil, coconut oil, cocoa butter, mango butter, evening primrose oil, black currant oil, avocado oil, and mixtures thereof. In another embodiment of the invention, the dilution comprises at least about 5%, 10%, 30%, 50%, 70% or 90% of the composition. In another embodiment of the invention, the dilution comprises at most about 10%, 30%, 50%, 70%, 90% or 95% of the composition. In another embodiment of the invention, the dilution comprises at least about 5%, 10%, 30%, 50%, 70% or 90% of the diluent oil. In another embodiment of the invention, the dilution comprises at most about 10%, 30%, 50%, 70% or 90%, or 95% of the diluent oil.

In another embodiment, the composition is diluted in grape seed oil. In another embodiment of the invention, the dilution comprises at least about 5%, 10%, 30%, 50%, 70% or 90% grape seed oil. In another embodiment of the invention, the dilution comprises at most about 10%, 30%, 50%, 70% or 90%, or 95% grape seed oil.

In another embodiment, the composition further comprises an essential oil selected from the group consisting of ajowan, almond oil, sweet almond oil, allspice, aloe vera oil, ammi visnaga (khella), amyris, angelica root, angelica seed, anise, anise seed, star anise, apricot kernel oil, absolute arnica, avocado oil, unrefined avocado oil, Copaiba balsam, balsam Peru genuine, balsam Peru oil, balsam peru liquid resin, balsam tolu, sweet french basil, basil, basil ct. methyl chavicol, lemon ct. citral basil, sweet ct. linalool basil, bay laurel, bay leaf, bay rum, bay leaf West Indies, bees wax, unrefined bees wax, benzoin absolute, benzoin resinoid, bergamot, mint bergamot, Italian bergamot oil, free bergaptene bergamot, birch, sweet birch, borage oil, boronia, butter, buchu leaf, cajeput, calamus, *calendula* oil, infused *calendula* oil, camellia oil, camphor, *cannabis*, caraway, caraway seed, cardamom, absolute carnation, carrot seed, high carotol carrot seed, carrot seed oil, *cassia*, cassis bud (black currant), castor oil, catnip, oil of catnip, cedarleaf, western red cedarleaf, cedarwood, Atlas cedarwood, Himalayan cedarwood, Virginia cedarwood, celery seed, chamomile, blue chamomile, German chamomile, Moroccan chamomile, Moroccan wild chamomile, Roman chamomile, champaca, cilantro, true cinnamon, cinnamon, cinnamon leaf, cinnamon *cassia*, cistus, citronella, Java citronella, ciste oil, artificial civet, clary sage, high sclareol clary sage, clementine, Italian clementine peel oil, clove, clove bud, clove, cocoa, cocoa butter, unrefined cocoa butter, coconut oil, refined coconut oil, cognac, coltsfoot, combava petitgrain, coriander, green coriander, cornmint, *costus* oil, cumin, cypress, davana oil, dill, dill weed, elemi, ephedra, erigeron (fleabane), *eucalyptus, eucalyptus citriodora, eucalyptus globulus*, lemon eucalyptus, fennel, sweet fennel, fenugreek, fir, fir needle oil, Canada fir needle, Siberia fir needle, white fir needle, frankincense, India frankincense, Oman frankincense, galbanum oil, garlic, genet, geranium, geranium leaf, geranium rose, Bourbon geranium, Egyptian geranium, ginger, Cochin extra ginger, ginsing, Siberian ginsing, Korean ginsing, grapefruit, pink grapefruit, white grapefruit, grapeseed oil, hazelnut oil, *helichrysum, helichrysum immortelle*, Mad. helichrysum, Balkan helichrysum, Corsica helichrysum, France helichrysum, hemp oil, absolute honeysuckle, hyssop, hyssop decumbens, absolute immortelle, fragrant aster inula, Jamaican gold, unrefined Jamaican gold, jasmine, absolute jasmine, grandiflorum jasmine, sambac jasmine, jojoba oil, helio-carrot in jojoba, melissa in jojoba, absolute jonquille, juniper berry, Siberia juniper berry, Croatia juniper berry, lanolin, unrefined anhydrous lanolin, *lantana camara*, laurel nobilis, lavandin, abrialis lavandin, grosso lavandin, lavender, Oregon lavender, Bulgarian lavender, Russian lavender, high-altitude lavendar, wild-crafted lavender, lavendin, organic lavindin, lemon, lemongrass, lime, distilled lime, expressed lime, *litsea, litsea cubeba*, blue, pink and white lotus, *macadamia* oil, mace, green mandarin, red mandarin, yellow mandarin, manuka, absolute marigold, marigold flower, marjoram, Spanish marjoram, sweet marjoram (true), massoia bark, *melissa*, codistilled *melissa*, "rectified" *melissa*, true *melissa*, menthol, methyl salicylate, absolute mimosa, *mimosa*, monarda, mugwort, musk seed, myrrh, myrtle, absolute narcissus, neroli (orange blossom), niaouli, nutmeg, extra nutmeg, oakmoss, absolute oak moss, olibanum, absolute opopanax, orange, bitter orange, blood orange, sweet orange, wild West Indian orange, oregano, orris root, concrete orris, osmanthus, palm oil, refined palm oil, palmarosa, paprika, parsley seed, patchouli, Indian patchouli oil, Indonesian patchouli oil, peanut, peanut oil, pecan oil, pennyroyal, pepper, black pepper, super black pepper, peppermint, India peppermint, USA baby mint peppermint, pet perfume, petitgrain (orange leaves), white pine, pine needle, evening primrose, *ravensara anisata*, true ravensara, ravensare, *ravintsara*, redberry, *rosalina*, rose, rose geranium, rose otto, Bulgarian rose, English rose, Turkish rose, rosehip seed oil, rosemary, rosemary anti-oxidant extract powder, rosemary verbenone, Morocco rosemary, Spain rosemary, rosewood, rosewood oil, rue, sage, white sage, sage dalmatian, sage officinalis, sage triloba, sandalwood, sassafras, seabuckthorn berry, sesame oil, sesame seed oil, shea butter, unrefined shea butter, spearmint, spikenard, green spikenard, spruce, St. John's wort, styrax resin, tagetes, tangerine, Dancy tangerine, tarragon, tea tree, Australia tea tree, *thuja* (cedar leaf), thyme, red thyme, thyme ct. linalool, thyme vulgaris, wild thyme, red thyme, thymol, mixed tocopherols, tolu balsam resin, absolute tuberose, tuberose, tumeric, valerian, vanilla, pure vanilla extract, vanilla bean, absolute vanilla bourbon, vegetable glycerin, absolute verbena, vetiver, violete leaves, vitex, organic Haiti vetiver, absolute violet leaf, walnut oil, wintergreen, natural wintergreen, wormwood, yarrow, ylang ylang, ylang ylang I, ylang ylang II, ylang ylang III, ylang ylang compound, ylang ylang complete, and ylang ylang extra; wherein the essential oil is in an amount of between about 0.1 to about 15 percent by weight of the total composition, in an amount of between about 0.5 to about 10 percent by weight of the total composition, in an amount of between about 5 to about 10 percent by weight of the total composition, and in an amount of between about 0.5 to about 5 percent by weight of the total composition.

In one embodiment of the invention, the composition may be stored in a sealed glass ampoule, multiuse bottle, or in an aerosol spray can. In one embodiment of this invention, the composition is stored in the presence of an inert gas. In another embodiment of the invention, the composition is stored in a container that maintains the composition in a substantially oxygen-free environment.

In another embodiment, the composition is packaged in one or more sealed glass ampoules in the presence of nitrogen gas. The composition may also be stored in a container that includes an integrated wiper tip or a brush tip.

In another embodiment of the invention, the composition may comprise an oil, serum, ointment, lotion, or cream for topical application that contains an effective amount of the composition. In these embodiments, the cream, ointment or paste should contain at least about 0.5% of the composition. In one embodiment, the cream, ointment, or paste may contain at least about 0.5%, 1%, 2% or 5% of the composition. In another embodiment, the cream, ointment, or paste may contain at most about 10%, 15%, 20%, 30%, or 50% of the composition.

This invention also relates to a method of using the composition to reduce or inhibit microbial growth. This invention also relates generally to a method using the composition to treat a fungal infection. The present invention also provides for a method using the composition to treat tinea corporis, capitis, corporis, manuum, pedis and onychomycosis. In another method of use, the composition is used to reduce or inhibit microbial growth due to tinea pedis, commonly known as athlete's foot.

In one embodiment of the invention, an effective amount of the composition is applied topically to a region of skin exhibiting microbial infection to reduce or inhibit microbial growth. In another embodiment of the invention, an effective amount of the composition is applied topically to a region of skin exhibiting microbial infection and then periodically re-applied to the same skin region to reduce or inhibit microbial growth.

In another embodiment, the composition is applied topically by brushing, wiping, or rubbing the composition on to the region of skin exhibiting microbial infection. In another embodiment of the invention, the composition is applied topically by brushing, wiping, or rubbing the composition on to the region of skin exhibiting microbial infection by use of a wiper tip or brush tip integrated with the container.

In another embodiment, an effective amount of the composition is applied topically to skin as a preventative measure to inhibit microbial growth. In another embodiment, the composition is applied topically to skin that is susceptible to microbial infection as a preventative measure. In another embodiment, the composition is applied topically to uninfected skin prior to exposing skin to an environment that poses a high risk of microbial infection, which may include locker rooms, public showers, sports facilities, and the like.

In another embodiment of the invention, the composition is applied to a surface to inhibit microbial growth. The composition may be sprayed, misted, or wiped on to a surface prone to microbial growth, which may include locker rooms, public showers, sports facilities, and the like.

These and other embodiments of the invention are described herein below or are evident to persons of ordinary skill in the art based on the following disclosures.

The above summary of the present invention is not intended to describe each embodiment or every implementation of the present invention. Advantages and attainments, together with a more complete understanding of the invention, will become apparent and appreciated by referring to the following detailed description and claims.

DETAILED DESCRIPTION OF THE INVENTION

Before the present compositions and methods are described, it is to be understood that this invention is not limited to the specific methodology, devices, compositions, and compositions described as such may, of course, vary. It is also to be understood that the terminology used herein is for the purpose of describing particular embodiments only, and is not intended to limit the scope of the present invention, which will be limited only by the appended claims.

It must be noted that as used herein and in the appended claims, the singular forms "a", "and", and "the" include plural referents unless the context clearly dictates otherwise.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All references, publications, patents, patent applications, and commercial materials mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

The invention provides for an antimicrobial composition obtained from plant materials, plant extracts, essential oils obtained from the plant materials, and synthetic compounds. The present invention relates generally to a composition of *origanum* oil in combination with additional plant materials, plant extracts, essential oils, or synthetic compounds that exhibits an anti-microbial effect. The antimicrobial composition contains a mixture of the oils or synthetic compounds in amounts effective to inhibit microbial growth.

In another embodiment of the invention, the composition exhibits anti-fungal effects. A fungus is any of the eukaryotic organisms of the kingdom Fungi (mycota), which lack chlorophyll and vascular tissue and range in form from a single cell (e.g., yeast) to a body of mass branched filamentous hyphae that often produce specialized fruiting bodies and pseudohyphae. The kingdom includes, but is not limited to, the yeasts, filamentous molds, dermatophytes, smuts, and mushrooms.

In some embodiments, the present invention is directed to a method of treating a fungal infection on an animal epidermis, nail or hair, or in an orifice of an animal. The method comprises contacting the fungus infection with a composition comprising one or more of the antimicrobial compositions of the present invention.

In some embodiments, the fungal infection is on an epidermis. In additional embodiments, the fungal infection is on a nail. In some of the invention methods, the fungal infection causes or aggravates tinea corporis, tinea pedis, tinea cruris, tinea unguium, tinea capitis, dandruff; a vaginal yeast infection, or diaper rash.

In some embodiments, the fungal infection is of a Malassezia furfur, a *Epidermophyton floccosum*, a *Trichophyton*, a *Dermatophilus congolensis*, a Microsporum, a Malassezia ovale, an *Aspergillus*, a *Blastomyces*, a *Candida*, a *Coccidioides*, a *Cryptococcus*, a *Histoplasma*, a Paracoccidioides, a *Sporothrix*, a Zygomycetes, a *Pseudallescheria*, a Scedosporum, or a Scopulariopsis.

The invention method can be used on any animal including a human, a nonhuman vertebrate such as a bird, or a nonhuman mammal. Examples of nonhuman vertebrates include any farm animal, for example a cow, a pig, a chicken, or a horse, or a companion animal such as a dog, a cat, a hamster, a gerbil, a guinea pig, a mouse, a rat, a potbellied pig, a ferret, or a caged bird.

The methods of the present invention are not narrowly limited to any particular method of contacting the compositions to the fungus infection. In some embodiments, the composition is applied directly on the fungal infected tissue. In other embodiments, the composition is applied to an article that comes in contact with the fungus infection. Examples of such articles include, but are not limited to, clothing, a towel, a comb, a brush, a diaper, bedding or bandages.

An advantage of using essential oils in comparison to the use of isolated or synthetic chemicals is the fact that essential oils are obtainable by simple processes, whereas the isolation or synthesis of pure chemicals requires more complicated processes, such as chromatographic separation.

*Origanum* oil is obtainable from the steam distillation and/or solvent extraction of plants such as *Origanum vulgaris* and *Origanum dictamnus*. *Origanum* oil consists primarily of carvacrol. The amount of carvacrol in *origanum* oil varies from about 70% to about 85%.

In addition to carvacrol, *origanum* oil can also contain aromadrine, cadinene, camphene, caryophelline, cymene, eucalyptol, geranial, limonene, linalool, myrcene, phellandrine, pinene, sabinene, terpinene, terpineol, terpinolene and thymol.

In one embodiment of this invention, *origanum* oil in combination with certain additional essential oils or synthetic components, results in a composition that is more effective as an antimicrobial than *origanum* oil alone. *Origanum* oil, which can be used as a food flavoring agent, possesses a broad spectrum of in vitro antimicrobial activities attributed to the high content of phenolic compounds, such as carvacrol. Without wishing to be bound by the theory, the antimicrobial activity of *origanum* oil is generally attributed to the presence of both phenolic compounds carvacrol and thymol. However, testing reveals that the presence of thymol is antagonistic to the antimicrobial effects of carvacrol. Without wishing to be limited by theory, it is believed that the high ratio of carvacrol to thymol in *origanum* oil minimizes the antagonistic effect of thymol.

A phenolic compound refers to any six-membered aromatic ring bonded directly to a hydroxyl (OH) group, such as carvacrol (5-isopropyl-2-methylphenol). The phenolic compounds may be added in an isolated form. Alternatively or additionally, essential oils containing the phenolic compounds as a major constituent may be added, with the final concentrations of the phenolic compounds being within the range of the invention. The term "major constituent" refers to those essential oils having phenolic compounds that constitute more than 50% by weight of the composition of the essential oil. It is well-known in the art that such essential oils may also contain lesser amounts of the other constituents. Essential oils including phenolic compounds as the major constituent include, for example, anise oil, bay oil terpeneless, clove bud oil, clove oil, clove oil, clove stem oil, *origanum* oil, Peru balsam oil, pimento oil, and thyme oil.

In one embodiment of the invention, the composition includes from about 80% to about 95% *origanum* oil and from about 5% to about 20% menthol.

Menthol, the common name for (1R,2S,5R)-2-isopropyl-5-methylcyclohexanol, is an example of a secondary alcohol. A secondary alcohol contains a hydroxyl group attached to a carbon which is directly attached to two alkyl groups.

Menthol can be produced synthetically or obtained through the distillation and/or solvent extraction of plants such as *Mentha arvensis* or *mentha piperita*. Menthol is commonly available as menthol crystals. After synthesis or steam distillation, the menthol-containing oils are cooled, which precipitates menthol to form menthol crystals. The menthol crystals may then be solubilized in an alcohol solution and added to the composition. Menthol has a variety of established uses, including as a topical analgesic or decongestant.

In another embodiment of the invention, the composition includes *origanum* oil and Atlantic cedarwood oil. In one embodiment of the invention, the composition includes from about 85% to about 99.9% *origanum* oil and from about 0.1% to about 10% Atlantic cedarwood oil.

Atlantic cedarwood oil is obtainable by the steam distillation of *Cedrus atlantica*—Moroccan Cedarwood. Atlantic cedarwood oil consists largely of the terpene molecules alpha-himachalene, beta-himachalene, and gamma-himachalene. Terpene molecules are hydrocarbons that consist of any number of isoprene units, or 2-methyl-1,3-butadiene. In addition to the terpene molecules, cedarwood oil may also consist of atlantone, bergamotene, cadinene, calacorine, caryophelline, cedrene, copaene, cubetine, farnesene, limonene, longiborneol (juniperol), longifolene, longipinene, pinene, terpineol, and thujopsene. Atlantic cedarwood oil can be used in perfumes and fragrances.

In another embodiment, the invention provides for a composition of *origanum* oil, menthol, and Atlantic cedarwood oil in the following ranges:
i. from about 70% up to about 98.9% *origanum* oil;
ii. from about 3% up to about 20% menthol; and
iii. from about 3% up to about 10% Atlantic cedarwood oil.

In another embodiment of this invention, the composition comprises about 85% *origanum* oil, about 10% menthol, and about 5% Atlantic cedarwood oil.

In one broad embodiment, the composition includes *origanum* oil and one or both of menthol and Atlantic cedarwood oil. In a further embodiment of the invention, the composition can also include the essential oils of *thuja*, cedarwood, cinnamon, clove, cumin, fennel, mint, peppermint, or rosemary. These preceding additives may be used individually or in combination.

In a broad embodiment of this invention, the composition comprises
i. from about 55% up to about 90% origanum oil;
ii. from about 3% up to about 20% menthol; and
iii. from about 3% up to about 10% Atlantic cedarwood oil.
iv. includes from as little as about 3% up to about 15% of the essential oils of at least one of the following: *thuja*, cedarwood, cinnamon, clove, cumin, fennel, mint, peppermint, or rosemary.

*Thuja* oil is obtainable by the steam distillation and/or solvent extraction of the twigs and leaves from the arborvitae *Thuja occidentalis*. The main constituent of *thuja* oil is the bicyclic terpene ketone (−)-1-Isopropyl-4-methylbicyclo [3.1.0]hexan-3-one, called thujone. *Thuja* oil also contains bornyl acetate, fenchone, the diterpene beyerene, sabinene, camphor and d-occidol.

Cedarwood oil is obtainable by the steam distillation of various cedarwood trees. Cedarwood is in the Conifer (Coniferae) Family along with other well-known trees such as Pine and Cypress. Cedarwood oil may be extracted from *Cedrus brevifolia*—Cyprian Cedar, *Cedrus virginiana*—American Cedarwood, *Cedrus deodara*—Himalayan Cedar, *Cedrus libani*—Lebanese Cedar, *Chamaecyparis thyoides*—Atlantic white cedarwood, *Chamaecyparis funebris*—Chinese cedar, *Juniperus virginiana*—Red Cedar, *Juniperus mexicana*—Texas cedar, *Juniperus virginiana, Thuja occidentalis*, the Western Red Cedar, and species of *Cupressus*. Cedarwood oil is often used in perfumes and fragrances and also in insect repellants.

Cinnamon oil is obtainable by the steam distillation of *Cinnamomum verum*. Cinnamon oil consists largely of two primary ingredients, namely cinnamic aldehyde (also known as cinnamal) and eugenol. Both of the aforementioned components exist naturally in cinnamon oil in varying concentrations determined by the particular source from which the cinnamon oil is derived. The cinnamic aldehyde ranges from about 50% to 90% by weight of the steam distillate of the bark. The eugenol content will ordinarily vary in distillate at from about 2% to 15% by weight.

Various other components also make up a minor portion of cinnamon oil or cinnamon leaf oil. These components include caryophyllene, 1-alpha-pinene, 1-linalool, benzaldehyde, benzyl benzoate, beta-phellandrene, camphene, camphor, chavicol, cinnamic alcohol, cinnamyl acetate, coumarin, cymene, furfural, limonene, methyl salicylate, myrcene, p-cymene, phellandrine, phenyl ethyl alcohol, sabinene, salicyaldehyde, safrole, tepinolene, terpinene, and terpineol. Cinnamon oil can be used as a food flavoring agent.

Clove oil is obtainable by the steam distillation of leaves from plants such as *Eugenia caryophyllata* and *Syzgium aromaticum*. Clove oil consists primarily of eugenol, ranging from 80-90% of the total composition, and also contains eugenyl acetate and caryophyllene. Clove oil can be used as a food flavoring agent and is commonly used in perfumes.

Cumin essential oil is obtainable by the steam distillation of the seeds of *Cuminum cyminum*. The main component of cumin essential oil is 4-isopropylbenzaldehyde or cuminaldehyde (>30%), together with smaller amounts of limonene, cuminol, pinene, terpineol, and beta-caryophyllene. Cuminaldehyde is commonly used in perfumes and other cosmetics.

Fennel essential oil is obtainable by the steam distillation of the seeds of *Foeniculum vulgare*. Fenchone, (−)-1,3,3-Trimethyl-2-norbornanone, is a constituent of Fennel oil. Fenchone is a ketone similar to camphor.

Rosemary oil is obtainable by the steam distillation of *Rosmarinus officinalis*. Rosemary oil contains: Cineole, Pinene, Borneol, Linalol, Alpha-Terpineol, Terpinen-4-ol, Bornyl Acetate, Camphor, Thujone, Camphene, Limonene, and Beta-Caryophyllene. Rosemary oil is commonly used in perfumes.

Peppermint oil is obtainable by vacuum distillation of *Mentha piperita*. The peppermint oil will create three fractions: a top fraction; a middle fraction; and a bottom fraction. During vacuum distillation, the first approximate 30% of the mint oil taken off is the top fraction, the next approximate 65% is the middle fraction, and the last approximate 5% is the bottom fraction. The various fractions have been found to be chemically distinct, for example the top and middle fractions contain substantially all of the l-menthol present in peppermint oil. Further, the bottom fraction contains a substantial amount of Germacrene-D. Germacrene-D is a terpene molecule that is used as an antimicrobial and insecticidal. In another embodiment of this invention, the peppermint oil additive is obtained from the bottom fraction after distillation. Peppermint oil is commonly used in the flavoring of oral hygiene products and chewing gum.

Mint oil is obtainable from the steam distillation of a variety of plants in the genus *Mentha* including: *Mentha×piperita; Mentha×gracilis; Mentha×rotundifolia*—False Applemint; *Mentha×smithiana*—Red Raripila Mint; *Mentha× villosa; Mentha×villosonervata*—Sharp-toothed Mint; *Mentha aquatica*—Water mint, or Marsh mint; *Mentha arvensis*—Corn Mint, Wild Mint, Japanese Peppermint, Field Mint, Pudina; *Mentha asiatica*—Asian Mint; *Mentha australis*—Australian mint; *Mentha canadensis; Mentha cervina*—Hart's Pennyroyal, *Mentha citrata*—Bergamot mint; *Mentha crispata*—Wrinkled-leaf mint, *Mentha cun-ninghamia; Mentha dahurica*—Dahurian Thyme; *Mentha diemenica*—Slender mint; *Mentha gattefossei*; Mentha grandora; *Mentha haplocalyx; Mentha japonica; Mentha kopetdaghensis; Mentha laxiflora*—Forest mint; *Mentha longifolia*—*Mentha sylvestris*, Horse Mint; *Mentha pulegium*—Pennyroyal; *Mentha requienii*—Corsican mint; *Mentha sachalinensis*—Garden mint; *Mentha satureioides*—Native Pennyroyal; *Mentha spicata*—*M. cordifolia*, Spearmint, Curly mint; *Mentha suaveolens*—Apple mint, Pineapple mint; and *Mentha vagans*—Gray mint. Mint oil is commonly used as a flavoring agent.

These various essential oil additives may be included to increase the specific or broad-spectrum antimicrobial activity, to achieve a required level of hypotoxicity or hypoallergenic activity, or to increase consumer acceptability or appeal. More specifically, the additives may be included to improve applicability, viscosity, or scent.

In one embodiment of this invention, the composition is undiluted. In another embodiment of this invention, the composition is diluted in an oil selected from the group consisting of almond oil, borage oil, canola oil, grape seed oil, jojoba oil, olive oil, soybean oil, sunflower oil, wheat germ oil, apricot kernel oil, carrot oil, coconut oil, cocoa butter, mango butter, evening primrose oil, black currant oil, avocado oil, and mixtures thereof. In another embodiment, the composition is diluted in grape seed oil.

In another embodiment of the invention, the dilution comprises from about 5% to about 90% of the *origanum* oil composition and from about 10% to about 95% of the diluent oil.

Another embodiment of this invention is to store the composition in the presence of an inert gas to prevent oxidation and increase the storage stability of the composition. Storage of the composition in the presence of a gas capable of oxidation will decrease the stability of the composition. Storage of the composition should ensure the freshness and purity of the composition and also allow for convenient use of the product.

In another embodiment, the composition is packaged in one or more sealed glass ampoules in the presence of nitrogen gas to prevent oxidation. Without wishing to be bound to any particular theory, essential oils may chemically interact with common plastics, thus compromising both the essential oil and the plastic storage container. Alternatively, glass containers are resistant to chemical interactions with essential oils.

A wiper tip or a brush tip integrated with the container can aid the consumer in applying the composition without wasting product or creating a mess. When stored in a container with an integrated wiper tip or brush tip, the composition may be topically applied directly from within the container. In another embodiment of the invention, the composition is packaged in glass ampoules containing a wiper tip for application of the composition.

In another embodiment, the composition comprises an oil, serum, ointment, lotion or cream and contains an effective amount of the composition. In another embodiment of the invention, the composition may comprise an oil, serum, ointment, lotion, or cream and contains an effective amount of the composition for topical application.

This invention also relates to a method of using the composition to reduce or inhibit microbial growth. This invention also relates generally to a method of using the composition to treat a fungal infection. The present invention also provides for a method of using the composition to treat tinea corporis, capitis, corporis, manuum, pedis and Onychomycosis. In another method of use, the composition is used to reduce or inhibit microbial growth due to tinea pedis, commonly known as athlete's foot.

In one embodiment of the invention, an effective amount of the composition is applied topically to a region of skin exhibiting microbial infection to reduce or inhibit microbial growth. In another embodiment of the invention, an effective amount of the composition is first applied topically to a region of skin exhibiting microbial infection and then periodically re-applied to reduce or inhibit microbial growth.

In another embodiment, the composition is applied topically by brushing, wiping, or rubbing the composition on to the region of skin exhibiting microbial infection. In another embodiment of the invention, the composition is applied topically by brushing, wiping, or rubbing the composition on to the region of skin exhibiting microbial infection by use of a wiper tip or brush tip integrated with the container.

The compositions used in the invention methods are not limited to any particular formulation, provided the formulation is pharmaceutically acceptable. By "pharmaceutically acceptable" it is meant a material that: (i) is compatible with the other ingredients of the composition without rendering the composition unsuitable for its intended purpose, and (ii) is suitable for use with subjects as provided herein without undue adverse side effects (such as toxicity, irritation, and allergic response). Side effects are "undue" when their risk outweighs the benefit provided by the composition. Non-limiting examples of pharmaceutically acceptable carriers include, without limitation, any of the standard pharmaceutical carriers such as phosphate buffered saline solutions, water, emulsions such as oil/water emulsions, microemulsions, nanoemulsions, and the like.

In other embodiments, the composition my be combined with other desirable components, including, optionally, ingredients discussed above such as a sweetener, an oil, an emulsifier, an emollient, a wetting agent, a detergent, a penetrant, alcohols, colorants, flavors, fragrances, preservatives, and/or carrier powder.

The use of particular excipients (detergents, oils, enzymes, etc.) can also function in the invention to increase the penetration of the substrate, the rate of penetration, the thoroughness of coverage, etc. These can also be used to cause the penetration of a spore or epidermis, hair or nails, or tissues of an orifice by an antifungal or antibacterial compound. Excipients can also be used to cause the spore to end dormancy and begin germination, thus making the spore more susceptible to the antifungal compound(s).

The composition comprising the antifungal or antibacterial compound can also include a compound to increase adherence to the epidermis, hair, nails or orifice. Increasing adherence can increase the length of time for which the compound remains in contact with the skin, hair and nails.

The above-described compounds can thus be formulated without undue experimentation for administration to a mammal, including humans, as appropriate for the particular application. Additionally, proper dosages of the compositions can be determined without undue experimentation using standard dose-response protocols.

Non-limiting examples of forms of the compositions include a cream, ointment, gel, liquid, solution, foam, powder, paste, gum, lacquer, shampoo, suspension, fog, spray, aerosol, pump spray, wipe or sponge.

In another embodiment, an effective amount of the composition is applied topically to skin as a preventative measure to inhibit microbial growth. Preventative use would occur before entering a high risk environment for tinea corporis, capitis, corporis, manuum, pedis or Onychomycosis or for those individuals with recurring infections.

In another embodiment of the invention, the composition is applied to a surface to inhibit microbial growth. The composition may be sprayed, misted, or wiped on to a surface prone to microbial growth, which may include locker rooms, public showers, sports facilities, and the like.

Without wishing to be bound to any particular theory, the body of evidence collected indicates these substances might work in a number of possible ways. Known or postulated activities include cytossolic hyperacidity, breakage of an electron transport chain, disruption of the cytoplasmic membrane, H+-ATPase inhibition, channel inhibition, and extracellular enzyme synthesis inhibition. Their action appears to be different from existing pharmaceutical treatments, which target metabolism.

Various concentrations and combinations of essential oils were screened to test for antifungal effectiveness. The following procedure was used for comparative in vitro efficacy studies involving different oil mixtures. The concentration of products exposed to the test fungus was 0.005%, a concentration lower then anticipated for clinical use in order to determine the relative inhibitory concentration.

*Trichophyton rubrum* is the fungus that is the most common cause of Tinea pedis. Cultures of *Trichophyton rubrum* (ATCC #28188) were cultured for approximately 7 days at 29° C. on Sabouraud Dextrose Agar. This was used as a source of inoculum. Stock preparations of each blend tested were prepared in ethanol (denatured, Acros). 0.10 g sample was transferred to 16 ml glass vials (National Scientific) and 10 ml ethanol was added. Vials were capped with septum caps with Teflon coated septa and shaken to dissolve.

TABLE 1

|  | Origanum | Menthol | Atlantic cedar wood | Cumin | Peppermint | Clove | Cinnamon |
|---|---|---|---|---|---|---|---|
| Example 1 | 100% | | | | | | |
| Example 2 | 85% | | 5% | 10% | | | |
| Example 3 | 90% | 10% | | | | | |
| Example 4 | 85% | 10% | 5% | | | | |
| Example 5 | 75% | 10% | 5% | | 10% | | |
| Example 6 | 75% | 10% | 5% | 10% | | | |
| Example 7 | 65% | 10% | 5% | 10% | | 10% | |
| Example 8 | 60% | 10% | 5% | 10% | | 10% | 5% |
| Example 9 | 55% | 10% | 5% | 10% | 10% | 10% | |

Various formulations of the composition shown in Table 1 were added to a concentration of 0.005% in test culture medium by the following process.

i. Autoclaved SDA was distributed into sterile schott bottles which were maintained in liquid form at 45° C. in a water bath;

ii. 20 ml of SDA was pipetted into a sterile empty culture tube. Immediately afterward, 0.1 ml of stock solution of the test mixture was transferred to the tube;

iii. The tube containing molten SDA and 0.1 ml stock solution was mixed by aseptically placing a square of freshly rolled out parafilm over the mouth the tube, followed by inverting 6 times;

iv. The contents of the tube were poured into sterile plastic petri dishes and allowed to solidify.

All plates were inoculated with test organism and incubated at 25° C. for approximately 8 days, then transferred to an incubator at 29° C. for further incubation.

In addition to the test cultures, controls were prepared under the same conditions and inoculated at the same time as the other cultures. The control cultures contained: a) SDA plus 0.1 ml ethanol (labeled alcohol control); b) SDA only (labeled medium control).

Evaluation was carried out by measuring colony diameters of individual cultures. Also, visual subjective growth comparisons were presented by photographing the cultures at selected time periods of growth, based on the condition of the medium and extent of the growth.

Referring to TABLE 2, it can be seen that Examples 1-9 all exhibit an antimicrobial effect against *Trichophyton rubrum*, relative to the two controls. Referring to TABLE 1, it can be seen that Examples 2, 3, 4, 5, 6, 7 and 8 all have a stronger antimicrobial effect than Example 1, which is 100% *origanum*. Referring to TABLE 2, it can be seen that Example 4 shows the strongest anti-microbial effect against *Trichophyton rubrum* at Day 20. Example 4 shows the strongest antimicrobial effect over Days 5, 7, 10, and 20.

TABLE 2

*Trichophyton rubrum* colony size (in millimeters)

|  | Day 5 | Day 7 | Day 10 | Day 20 |
| --- | --- | --- | --- | --- |
| Alcohol control | 12 | 16 | 29 | 51 |
| Medium control | 12 | 16 | 29 | 49 |
| Example 1 | 7 | 9 | 22 | 38 |
| Example 2 | 5 | 7 | 22 | 36 |
| Example 3 | 4 | 5 | 17 | 33 |
| Example 4 | 4 | 5 | 17 | 31 |
| Example 5 | 5 | 6 | 22 | 36 |
| Example 6 | 5 | 5 | 22 | 36 |
| Example 7 | 5 | 5 | 18 | 38 |
| Example 8 | 5 | 5 | 18 | 32 |
| Example 9 | 5 | 8 | 25 | 41 |

REFERENCES

1. "Antifungal activities of *origanum* oil against *Candida albicans*." Mol Cell Biochem. 2001 December; 228(1-2): 111-7.
2. "Activity of thymol, carvacrol, cinnamaldehyde and eugenol on oral bacteria." Pharm Acta Hely. 1994 July; 69(1):25-8.

The invention claimed is:

1. A composition comprising at least 50% of one or more phenolic compound and at least 15% of one or more secondary alcohol in an amount effective as an antimicrobial agent, wherein the phenolic compound is *origanum* or thyme oil; and wherein the secondary alcohol is menthol.

2. The composition according to claim 1, wherein the phenolic compound is carvacrol or thymol.

3. The composition according to claim 1, wherein the menthol is derived from menthol oil, menthol crystals or a synthetic product.

4. The composition according to claim 3, wherein the composition comprises at most 85% *origanum* or thyme oil.

5. The composition according to claim 4, wherein the composition comprises at least 50% carvacrol or thymol.

6. The composition according to claim 1, wherein the phenolic compound is *origanum* oil and wherein the *origanum* oil comprises a ratio of carvacrol to thymol high enough to minimize the antagonistic effect of thymol.

7. The composition according to claim 3, wherein the composition comprises at most 70% carvacrol or thymol.

8. The composition according to claim 1, wherein the composition comprises at most 80% carvacrol or thymol.

9. The composition according to claim 1, wherein the composition comprises at least 60% carvacrol or thymol.

10. The composition according to claim 3, further comprising at least one agent, in which the agent is chosen from anti-inflammatory, skin permeant, vasodilator, and antibiotic agents.

11. The composition according to claim 10, wherein the composition is adapted for application to hooves, nails, skin, or combinations thereof.

12. A method for reducing or inhibiting microbial growth in a subject, said method comprising topically applying the composition according to claim 3 to the subject in need thereof.

13. A method for reducing or inhibiting microbial growth in a subject, said method comprising topically applying the composition according to claim 5 to the subject in need thereof.

14. A method for reducing or inhibiting microbial growth in a subject, said method comprising topically applying the composition according to claim 1 to the subject in need thereof.

15. A method for reducing or inhibiting microbial growth in a subject, said method comprising topically applying the composition according to claim 8 to the subject in need thereof.

16. A method for treating tinea corporis, capitis, corporis, manuum, pedis or onychomycosis in a subject, said method comprising topically applying the composition according to claim 3 to the subject in need thereof.

17. A method for treating tinea corporis, capitis, corporis, manuum, pedis or onychomycosis in a subject, said method comprising topically applying the composition according to claim 5 to the subject in need thereof.

18. A method for treating tinea corporis, capitis, corporis, manuum, pedis or onychomycosis in a subject, said method comprising topically applying the composition according to claim 1 to the subject in need thereof.

19. A method for treating tinea corporis, capitis, corporis, manuum, pedis or onychomycosis in a subject, said method comprising topically applying the composition according to claim 8 to the subject in need thereof.

20. A method for treating fungal infection in a subject, said method comprising topically applying the composition according to claim 11 to the hooves, nails, skin, or combinations thereof in the subject in need thereof.

21. The method according to claim 20, wherein the fungal infection afflicts dermal tissue, subdermal tissue, mucosal membranes, or combinations thereof.

22. The method according to claim 20, wherein the fungal infection is tinea pedis, onychomycosis, tinea cruris, tinea corpora, candidiasis, tinea versicolor, aspergillosis, coccidiodomycosis, cryptococcal meningitis, histoplasmosis, hoof thrush, hoof rot, or combinations thereof.

\* \* \* \* \*